United States Patent
Curran et al.

(10) Patent No.: US 11,280,757 B2
(45) Date of Patent: Mar. 22, 2022

(54) FAECAL DETECTION SENSOR

(71) Applicant: FRED BERGMAN HEALTHCARE PTY LTD, New South Wales (AU)

(72) Inventors: Peter Curran, New South Wales (AU); Mehdi Azimi, New South Wales (AU); Hadi Mashin-Chi, New South Wales (AU); Peter Aigner, New South Wales (AU); Juuso Olkkonen, Espoo (FI); Anna-Marja Aura, Espoo (FI); Anu Vaari, Espoo (FI); Antti Nyyssola, Helsinki (FI); Lisa Hakola, Espoo (FI); Maria Smolander, Espoo (FI)

(73) Assignee: FRED BERGMAN HEALTHCARE PTY LTD, New South Wales (AU)

( * ) Notice: Subject to any disclaimer, the term of this patent is extended or adjusted under 35 U.S.C. 154(b) by 421 days.

(21) Appl. No.: 16/079,452

(22) PCT Filed: Feb. 23, 2017

(86) PCT No.: PCT/AU2017/050157
§ 371 (c)(1),
(2) Date: Aug. 23, 2018

(87) PCT Pub. No.: WO2017/143396
PCT Pub. Date: Aug. 31, 2017

(65) Prior Publication Data
US 2020/0256819 A1  Aug. 13, 2020

(30) Foreign Application Priority Data
Feb. 23, 2016  (AU) .................... 2016900631

(51) Int. Cl.
*G01N 27/327*  (2006.01)
*C12Q 1/00*  (2006.01)
*A61F 13/42*  (2006.01)

(52) U.S. Cl.
CPC .......... *G01N 27/3271* (2013.01); *A61F 13/42* (2013.01); *C12Q 1/001* (2013.01); *A61F 2013/424* (2013.01)

(58) Field of Classification Search
CPC ...................... G01N 27/3271; A61F 13/42; A61F 2013/424
See application file for complete search history.

(56) References Cited

U.S. PATENT DOCUMENTS

| | | | |
|---|---|---|---|
| 4,152,235 A * | 5/1979 | Dobson | G01N 27/333 204/406 |
| 7,364,872 B1 * | 4/2008 | Hainfeld | B82Y 5/00 204/403.04 |

(Continued)

FOREIGN PATENT DOCUMENTS

| WO | 2013016765 A1 | 2/2013 |
|---|---|---|
| WO | 2014098690 A1 | 6/2014 |

OTHER PUBLICATIONS

A. Wieckowska, Structuring of supported hybrid phospholipid bilayers on electrodes with phospholipase A2, Phys. Chern. Chem. Phys., 2011, 13, p. 9716-24. (Year: 2011).*

(Continued)

*Primary Examiner* — Luan V Van
*Assistant Examiner* — Caitlyn Mingyun Sun
(74) *Attorney, Agent, or Firm* — Millen, White, Zelano & Branigan, P.C.; William Nixon

(57) ABSTRACT

The invention provides the present invention provides a faecal detection sensor for an absorbent article. The sensor includes a faeces-sensitive material that reacts to the presence of a constituent of faecal matter, wherein the sensor exhibits an electrical property that changes following the reaction of the faeces-sensitive material. In embodiments of the invention the faeces sensitive material is a material that reacts due to the presence of a sulfur-containing compound in faecal matter, such as metallic faeces-sensitive materials, (Continued)

or is a material that reacts with a faecal enzyme and/or other constituents of faecal matter, such as organic faeces-sensitive materials.

27 Claims, 11 Drawing Sheets

(56) References Cited

U.S. PATENT DOCUMENTS

| | | | |
|---|---|---|---|
| 9,188,556 B2* | 11/2015 | Sun | A61B 5/1486 |
| 2002/0019615 A1 | 2/2002 | Roe | |
| 2007/0142799 A1* | 6/2007 | Ales | A61L 15/56 |
| | | | 604/361 |
| 2010/0175991 A1* | 7/2010 | Shimomura | C12Q 1/001 |
| | | | 204/403.1 |
| 2012/0109087 A1 | 5/2012 | Abraham | |
| 2014/0296808 A1* | 10/2014 | Curran | G01N 27/225 |
| | | | 604/361 |
| 2015/0008142 A1* | 1/2015 | Jeon | C12Q 1/54 |
| | | | 205/777.5 |
| 2015/0144505 A1* | 5/2015 | Elder | A61B 5/05 |
| | | | 205/777.5 |
| 2015/0192537 A1* | 7/2015 | Sekimoto | G01N 27/3272 |
| | | | 204/403.14 |

OTHER PUBLICATIONS

C. Ballot, Lipase assay in duodenal juice using a conductometric method, Clinica Chimica Acta, 1984, p. 109-14. (Year: 1984).*
Y. Wang, Properties of a Triacetin Molecule under an External Electric Field, IEEE, 2016, p. 1-4 (Year: 2016).*
Chapter 2 Conductometry (Year: 2021).*
Triacetin_C9H14O6_PubChem. (Year: 2021).*
Tristearin_C57H110O6_PubChem (Year: 2021).*
International Search Report PCT/AU2017/050157 dated May 30, 2017.

* cited by examiner

FAECAL DETECTION SENSOR

TECHNICAL FIELD

The present invention relates to a sensor, a system and a method for detecting the presence of faecal matter in an incontinence garment, pad, diaper, or the like for automated monitoring and alerting of faecal voiding or incontinence events.

BACKGROUND OF INVENTION

Enzymes including lipases and proteases are prevalent in faecal matter. Presently, faecal matter from a subject can be analysed for use in diagnostics by measuring specific enzyme levels. For example, faecal enzyme assays are used to measure levels of specific enzymes which are related to chronic diseases such as pancreatic insufficiency in cystic fibrosis, HIV, celiac disease, inflammatory bowel disease and syndrome, and diabetes mellitus. These diseases may cause elevation of protease (e.g. elastase and trypsin) and lipase enzymes in faecal matter.

In addition to enzymes, sulfur-containing compounds are also present in faecal matter. Some of the sulfur-containing compounds that are present in faecal matter include methanethiol, dimethyl disulfide, dimethyl trisulfide, and $H_2S$.

Elevated levels of lipases and proteases in faecal matter contribute to skin irritation. Incontinence, including faecal incontinence, is a common condition among the elderly, as well as in infants and young children. Generally the longer that faecal matter is left in contact with skin the higher the likelihood of skin integrity problems and related infections, particularly in the elderly where skin, with age, becomes less supple, thinner, and drier and is more easily injured and is slower to heal.

Accordingly, a reliable and responsive means for the detection and alerting of faecal events in an incontinence garment, pad, diaper, or the like worn by a subject is desirable.

Furthermore, it is desirable that such a sensor responds within an acceptable time from the occurrence of the detected faecal event and said response is efficiently communicated via an alert system to the subject or carer to take appropriate action.

The discussion of the background to the invention included herein including reference to documents, acts, materials, devices, articles and the like is included to explain the context of the present invention. This is not to be taken as an admission or a suggestion that any of the material referred to was published, known or part of the common general knowledge in any country as at the priority date of any of the claims.

SUMMARY OF INVENTION

Accordingly, in one aspect, the present invention provides a faecal detection sensor for an absorbent article, the sensor including: a conductive element and a faeces-sensitive material, insulating, at least in part, the conductive element wherein the sensor exhibits an electrical property that changes following a reaction of the faeces-sensitive material to the presence of a constituent of faecal matter.

As will become apparent from the foregoing, embodiments of the invention include a conductive element which may, or may not, be comprised of a faeces sensitive material of which some embodiments include a faeces-sensitive material that covers, at least in part, the conductive element.

Accordingly, in some embodiments, the conductive element only is comprised of a faeces sensitive material, in other embodiments only the material covering the conductive element is comprised of a faeces sensitive material and in other embodiments both the conductive element and the material that covers, at least in part, the conductive element are comprised of two different faeces sensitive materials.

A faeces-sensitive material, in accordance with embodiments of the invention, is a material that reacts due to the presence of a sulfur-containing compound in faecal matter, in which case they are metallic faeces-sensitive materials, or a faecal enzyme and/or other constituents of faecal matter, in which case they are organic faeces-sensitive materials, that are not at all present, or are not present to a substantial degree, in urine or sweat or other bodily fluids or discharges.

The term react, as it is used herein to define a property of faeces sensitive materials occurring due to the presence of a constituent of faecal matter in accordance with the invention, includes a chemical reaction of the faeces sensitive material that results is a change in an electrical property of the sensor. As will become apparent from the foregoing description, the type of reaction of a material that will occur depends on the type of faeces sensitive material. For example, if the faeces sensitive material is a material, such as silver metal or an alloy of silver, that reacts with a sulfur-containing compound present in faecal matter then react includes a chemical reaction of the faeces sensitive material resulting from a chemical reaction of the material (e.g. silver) with the sulfur-containing compound forming a high resistance sulphide layer, such as silver sulphide. If the faeces sensitive material is a material, such as a lipid or any lipid embodiments disclosed herein, that reacts with a faecal enzyme then react includes a break-down or chemical deterioration of the material (e.g. lipid) resulting from a chemical reaction with the faecal enzyme.

In embodiments, the faeces-sensitive material covers, at least in part, the conductive element. Preferably, the conductive element is comprised of a metallic faeces sensitive material covered by an organic faeces-sensitive material that acts as an insulator to electrically and chemically insulate the metallic faeces-sensitive material.

In embodiments, the faeces-sensitive material covers, at least in part, a conductive element, which conductive element is not comprised of a faeces sensitive material. The conductive element can be comprised of a metallic material that is not faeces sensitive that is covered by an organic faeces-sensitive material that acts as an insulator to electrically and chemically insulate the metallic conductive element.

Preferably, the faeces-sensitive material covering, at least in part, the conductive element acts as an insulator to electrically insulate and/or chemically insulate the conductive element.

Preferably, the faeces-sensitive material breaks down due to the presence of the constituent of faecal matter.

Preferably, the reaction of the faeces-sensitive material covering, at least in part, the conductive element exposes the conductive element to faecal or other matter.

Preferably, the faeces-sensitive material covering, at least in part, the conductive element is a material that reacts to the presence of a faecal lipase or protease. In embodiments, the faeces-sensitive material covering, at least in part, the conductive element includes a lipid, preferably a triglyceride. The faeces-sensitive material covering, at least in part, the conductive element can include tristearin (glyceryl tristearate, 1,3-di(octadecanoyloxy)propan-2-yl octadecanoate). In embodiments, the faeces-sensitive material covering, at least in part, the conductive element is a combination of tristearin and stearic acid.

The sensor can include a conductive element including electrodes that are electrically insulated from each other by the preferably organic faeces-sensitive material covering, at least in part, the conductive element. Preferably, the electrical property that changes following the reaction of the preferably organic faeces-sensitive material is an electrical resistance between the electrodes. In embodiments, the reaction of the preferably organic faeces-sensitive material allows ingress of faecal or other matter between the electrodes.

In embodiments, the conductive element is comprised of a faeces sensitive material that reacts to the presence of another constituent of faecal matter.

The conductive element can comprise material that is selected to react to the presence of sulfur-containing compounds including any one of more of methanethiol, dimethyl disulfide, dimethyl trisulfide, and/or H2S.

The conductive element is preferably comprised of silver or a silver alloy.

In embodiments, the electrical property that changes following the reaction of the faeces-sensitive material is electrical resistance of the conductive element which preferably increases as a consequence of the reaction with the sulfur-containing compounds.

The sensor can include electrodes that are electrically insulated from each other by an insulator that is not sensitive to faeces. Preferably, the electrical property that changes following the reaction of the preferably organic faeces-sensitive material is capacitance between the electrodes. The faecal matter acts, at least in part, to change the permittivity of the dielectric between the electrodes and a corresponding change in the electric field and capacitance between the electrodes.

In embodiments, the change in the electrical property is a difference in the resistance between the electrodes when the preferably organic faeces-sensitive material is between the electrodes and when the reaction of the preferably organic faeces-sensitive material allows ingress of faecal or other matter between the electrodes.

Preferably, the conductive element includes electrodes covered, at least in part, by the faeces-sensitive material which acts as a dielectric.

Preferably, the conductive element includes electrodes that are electrically insulated from each other by an insulator that is not sensitive to faeces.

Preferably, the electrical property that changes following the reaction of the faeces-sensitive material is capacitance between the electrodes.

The faecal detection sensor can further include a layer of nonwoven material covering the faeces-sensitive material. In embodiments, the faeces-sensitive material is impregnated into the nonwoven material.

In embodiments, the faecal detection sensor is configured for wireless detection of the electrical property.

The faecal detection sensor can include a resonant circuit that is adapted to resonate at a characteristic frequency in response to an interrogating signal from an external interrogating device whereby the resonance characteristic of the resonant circuit is indicative of the electrical property, which changes in the presence of faecal matter. In an embodiment, the sensor includes a second resonant circuit that is adapted to remain unaffected by the presence of faeces, urine or sweat and continue to resonate at a characteristic frequency in response to an interrogating signal from an external interrogating device regardless of the presence of faeces, urine or sweat. The second resonant circuit acts as a means for verification that the sensor is within range of the interrogating signal of the interrogating device.

Preferably, the faecal detection sensor is configured for use with an absorbent article such as a diaper or nappy.

In another aspect, the invention provides a system for detecting the presence of faecal material in an absorbent article. The system includes a faecal detection sensor locatable on an inner patient facing surface of an absorbent article. The sensor includes a faeces-sensitive material that insulates, at least in part, a conductive element, wherein the sensor exhibits an electrical property that changes following the reaction of the faeces-sensitive material in the presence of a constituent of faecal matter. The system preferably includes a device for monitoring the electrical property of the sensor element and thereby detecting any change in the electrical property that occurs following reaction of the faeces-sensitive material.

The system for detecting the presence of faecal material in an absorbent article of the above aspect of the invention preferably includes the sensor, and any one of the embodiments thereof, described above.

In yet another aspect, the present invention provides a method for detecting the presence of faecal matter in an absorbent article. The method includes monitoring an electrical property of a faecal detection sensor in an absorbent article including a faeces-sensitive material that insulates, at least in part, a conductive element, and detecting a change in the electrical property following the reaction of the faeces-sensitive material to the presence of faecal matter.

The step of detecting the change in the electrical property can include measuring a change in electrical resistance of the preferably metallic faeces sensitive conductive element occurring as a consequence of the reaction with sulfur-containing compounds in the faecal matter.

The step of detecting the change in the electrical property can include measuring a change in electrical resistance between electrodes electrically insulated from each other by the preferably organic faeces-sensitive material occurring as a consequence of the reaction of the preferably organic faeces-sensitive material.

The step of detecting the change in the electrical property can include measuring a change in electrical capacitance between electrodes electrically insulated from each other occurring as a consequence of the reaction of the faeces-sensitive material.

The method can further include a step of monitoring the electrical property of the sensor element and thereby detecting any change in the electrical property that occurs following reaction of the faeces-sensitive material.

BRIEF DESCRIPTION OF DRAWINGS

The present invention will now be described in more detail with reference to embodiments of the invention illustrated in the figures, wherein.

DETAILED DESCRIPTION

As will become apparent from the foregoing, embodiments of the invention include a faecal detection sensor including a faeces-sensitive material that reacts to the presence of a constituent of faecal matter, wherein the sensor exhibits an electrical property that changes following the reaction of the faeces-sensitive material. In embodiments, the faeces sensitive material may be comprised of a conductive element formed of faeces sensitive material, such as a metallic faeces sensitive material. In other embodiments, the faeces sensitive material may be comprised of a layer of preferably organic faeces sensitive material that directly or indirectly covers, at least in part, a conductive element, which conductive element may or may not be comprised of a preferably metallic faeces sensitive material. Accordingly, in embodiments, the conductive element only is comprised of a preferably metallic faeces sensitive material, in other embodiments, only the material covering the conductive element is comprised of a preferably organic faeces sensitive material and in other embodiments both the conductive element and the material that covers, at least in part, the conductive element are comprised of preferably metallic and organic faeces sensitive materials respectively.

Figure 1:
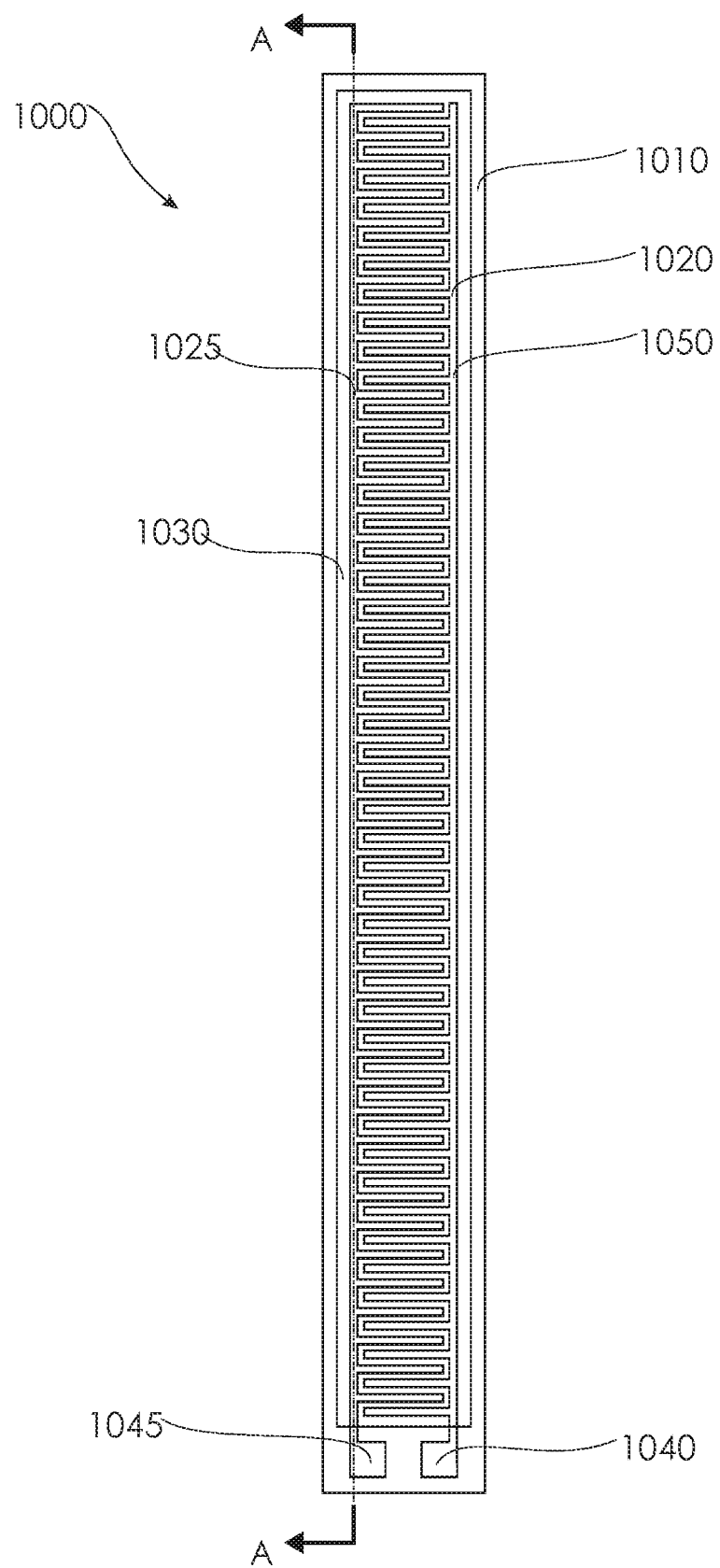
FIG. 1 illustrates a schematic plan view of a faecal detection sensor in accordance with an embodiment of the invention comprising a pair of electrodes on a substrate that are electrically insulated from each other by the organic faeces-sensitive material which, upon reaction to faecal matter, results in a change in electrical resistance between the electrodes.
Figure 2:
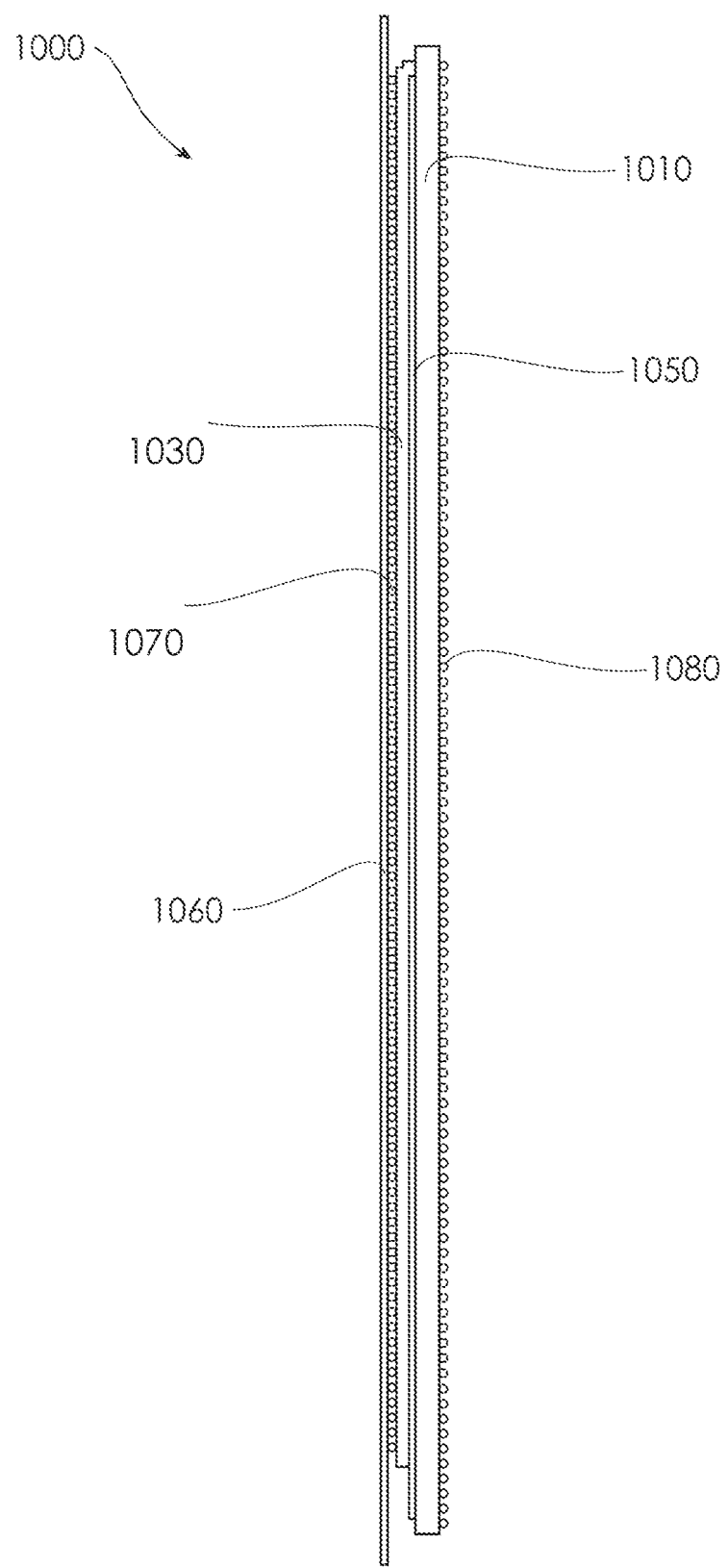
FIG. 2 illustrates a schematic side view of the faecal detection sensor of FIG. 1 showing the layering of the components of the sensor including a substrate, a conductive layer including electrodes, organic faecal sensitive material, a nonwoven material layer and an adhesive for adhering the sensor to an absorbent garment.

FIGS. 1 and 2 illustrate a faecal detection sensor 1000 in accordance with an embodiment of the present invention. The sensor 1000 includes a faeces-sensitive material 1030 that reacts to the presence of a constituent of faecal matter that is preferably not present in urine and sweat such as a sulfur-containing compound including any one or more of methanethiol, dimethyl disulfide, dimethyl trisulfide and $H_2S$ and/or a faecal enzyme. The sensor 1000 exhibits an electrical property that changes following the reaction of the faeces-sensitive material 1030. In embodiments, the electrical property may be any one or more of electrical resistance, capacitance or voltage.

The faecal detection sensor 1000 is fabricated on a faecal detection sensor substrate 1010. The faecal detection sensor substrate 1010 comprises a layer of an organic polymer. In some embodiments, the faecal detection sensor substrate 1010 is a layer with a thickness in a range from 10 micrometres to 1500 micrometres. In one embodiment of the invention, the faecal detection sensor substrate 1010 is a layer of poly(ethylene terephthalate) (PET), preferably with a thickness in a range from 50 micrometres to 500 micrometres. In another embodiment of the invention, the faecal substrate 1010 is a layer of paper or other form of cellulosic material preferably with a thickness in a range of 80 micrometres to 1000 micrometres. In a preferred embodiment, the faecal detection sensor substrate 1010 is a layer of poly(ethylene terephthalate) (PET) with a thickness in a range from 100 micrometres to 200 micrometres.

The faecal detection sensor 1000 comprises two faecal detection sensor electrodes 1020, 1025 fabricated as part of a conductive layer 1050 on the top surface of the faecal detection sensor substrate 1010. In the embodiment illustrated in FIGS. 1 and 2, the faecal detection sensor electrodes 1020, 1025 have a mutually interdigitated geometry. Also incorporated in the conductive layer 1050 are two faecal detection sensor terminals 1040, 1045. Each of the faecal detection sensor electrodes 1020, 1025 is in electrical contact with a respective one of the faecal detection sensor terminals 1040, 1045.

Figure 2A:
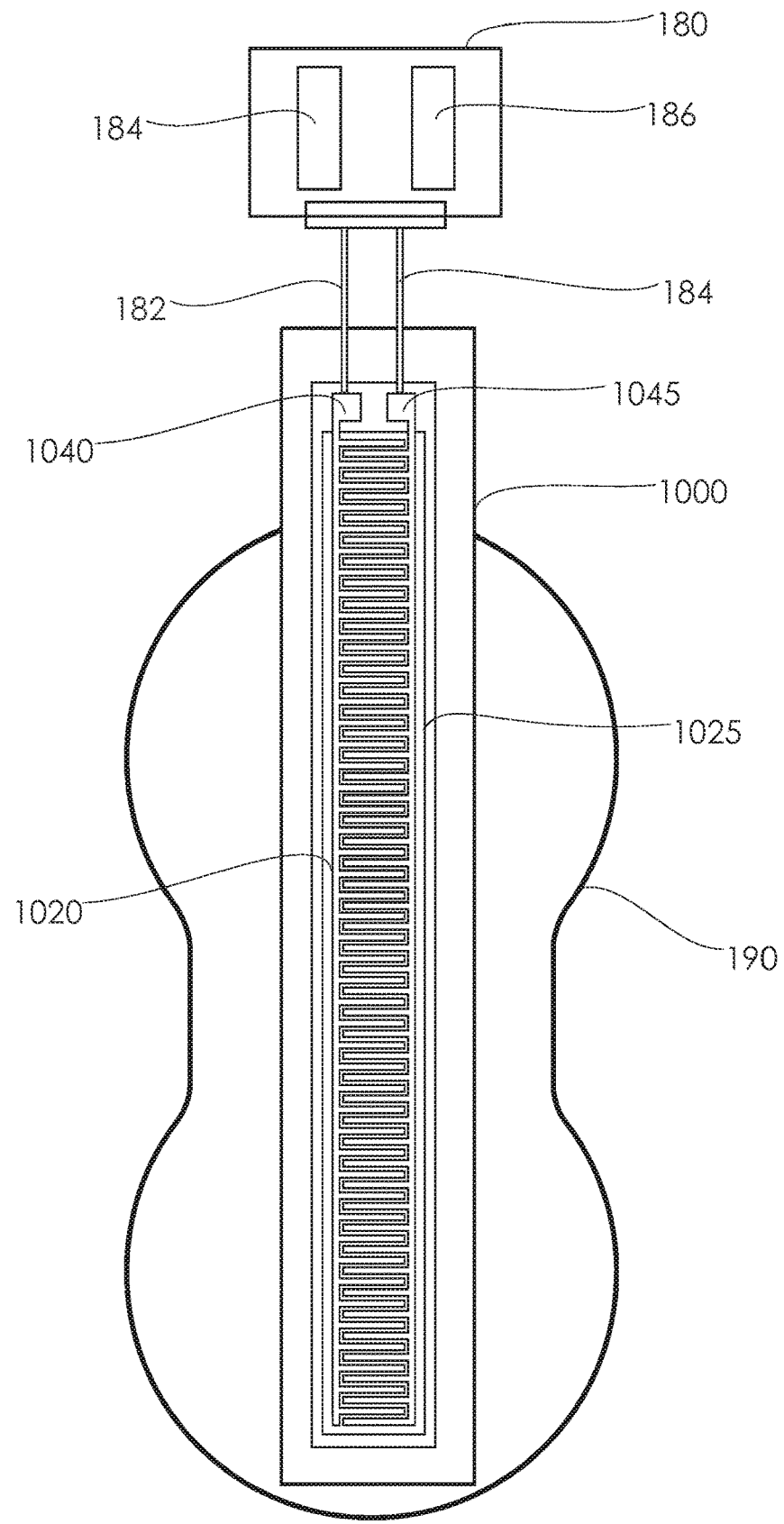
FIG. 2A illustrates an embodiment of a combination absorbent article, the faecal detection sensor of FIGS. 1 and 2 and an electronic device connected thereto.

FIG. 2A illustrates how, during use of the faecal detection sensor 1000 in an absorbent article 190, the faecal detection sensor terminals 1040, 1045 are used to establish electrical connectivity with a device 180 that is adapted for monitoring one or more electrical properties of the faecal detection sensor 1000 and, in particular, of the electrodes 1020, 1025 such as resistance, voltage or capacitance between the electrodes 1020, 1025. The device includes a processor 184 and a transmitter/receiver 186. The electronic device 180 includes one or more electrical connectors 182, 184 for physical connection with the sensor terminals 1040, 1045. The electronic device 180 is adapted to transmit and receive signals, preferably wirelessly, to a remotely located receiver (not shown). The processor 184, alone or in combination with another remotely located processor, determines and/or measures one or more electrical properties (e.g. resistance, voltage or capacitance) of the element or circuit comprising the electrodes 1020, 1025 between the faecal detection sensor terminals 1040, 1045. The processor 184, alone or in combination with another remotely located processor, process the determined and/or measured electrical properties of the element, transmit the determined and/or measured electrical properties, or information indicative thereof, to a communications relay subsystem or directly to a server, transmit the processed electrical properties, or information indicative thereof, to a communications relay subsystem or directly to a server, and/or receive data and/or commands from a communications relay subsystem or directly from a server.

In some embodiments, the conductive layer 1050, which includes the electrodes 1020, 1025 is fabricated by screen-printing the conductive layer 1050 on the top surface of the substrate 1010 and then curing the conductive layer 1050. Alternatively, the conductive layer 1050 is fabricated via piezoelectric inkjet printing of conductive material and subsequent UV curing thereof. Alternatively, the conductive layer 1050 is fabricated via evaporation and patterning of the conductive layer 1050 or via sequential evaporation and patterning of a plurality of the conductive layers 1050 on the top surface of the faecal detection sensor substrate 1010.

In an embodiment, the conductive layer 1050, including the electrodes 1020, 1025, has a thickness in a range from 10 nanometres to 200 micrometres. In an embodiment of the invention, conductive layer 1050, including the electrodes 1020, 1025, is comprised of a layer of gold with a thickness in a range from 10 nanometres to 100 micrometres. In another embodiment of the invention, the conductive layer 1050, including the electrodes 1020, 1025, is a layer of gold with a thickness in a range from 10 nanometres to 100 nanometres.

In the embodiment illustrated in FIGS. 1 and 2, the faecal detection sensor electrodes 1020, 1025 are covered directly by a layer 1030 of the preferably organic faeces-sensitive material. The layer of faeces-sensitive material 1030 is preferably comprised of, or includes, an insulator material that reacts to the presence of a faecal enzyme and/or other faecal constituents but is substantially insensitive to other bodily fluids, like, urine and sweat. The organic faeces-sensitive material layer 1030 can include a material selected to react to the presence of the lipase enzymes that are present in faecal matter and may include a lipid. In embodiments of the invention, the organic faeces-sensitive material 1030 includes a triglyceride. The organic faeces-sensitive material layer 1030 can include tristearin (glyceryl tristearate, 1,3-di(octadecanoyloxy)propan-2-yl octadecanoate). Other faeces-sensitive materials may alternatively be used in the organic faeces-sensitive material layer 1030 that reacts with one or more specific components within faeces. However, it has been found that the preferred materials for the organic faeces-sensitive material layer that are disclosed herein have properties that make them superior over other alternatives including that they provide a sensor that responds within an acceptable time, preferably from 4 to 6 minutes and/or preferably less than 5 minutes, after coming into contact with faecal matter upon the occurrence of the detected faecal event.

Tristearin has a melting point between 54 degrees Celsius to 72.5 degrees Celcius. For storage and handling purposes, a melting point higher than the lower end of the range may be more desirable. This may be achieved, in some embodiments of the invention, where the organic faeces-sensitive material is a combination of two or more material. In some of the embodiments of the invention, the organic faeces-sensitive material layer 1030 includes a combination of tristearin that melts at 54 degrees Celcius and stearic acid, which has a melting point of 69.3 degrees Celcius. This material combination has a melting point that is advantageously higher than 54 degrees Celcius. In some of the embodiments of the invention the organic faeces-sensitive material layer 1030 is a combination of tristearin that melts at 65 degrees Celcius and stearic acid, which has a melting point of 69.3 degrees Celcius. This material combination has a melting point that is advantageously higher than 65 degrees Celcius.

As illustrated in FIG. 2A and described above, in use, the faecal detection sensor 1000 is attached to a garment, which may include an absorbent garment such as a diaper or incontinence garment, worn by a subject, who is being monitored by a system incorporating the faecal detection sensor 1000. The faecal detection sensor 1000 is attached to such a garment in such a manner that the organic faeces-sensitive material layer 1030 would come into contact with any faecal matter but that the faecal detection sensor terminals 1040, 1045 would not come into contact with any faecal matter.

Referring to FIG. 2, an optional nonwoven layer 1060 is attached to the top surface of the faecal detection sensor 1000 via an adhesive layer 1070. The top surface of the faecal detection sensor 1000 is defined in this context as being the surface that is proximal the organic faeces-sensitive material layer 1030. The adhesive layer 1070 also optionally provides a means of attachment of the faecal detection sensor 1000 to the garment. During use, the nonwoven layer 1060 would be substantially in contact with the skin of the subject wearing the garment, and the main purpose of the nonwoven layer 1060 is to provide a measure of comfort to the subject wearing the combination garment and faecal detection sensor 1000. A pressure sensitive adhesive layer 1080 is optionally provided on the back surface of the faecal detection sensor 1000 to provide another potential means of attachment of the faecal detection sensor 1000 to the garment. The back surface of the faecal detection sensor 1000 is defined in this context as being the surface that is proximal the substrate 1010. The nonwoven layer 1060 has an areal density that is in a range between 5 grams per square metre and 100 grams per square metre.

In another embodiment, the functionality of the organic faeces-sensitive material layer 1030 and the nonwoven layer 1060 can be combined into one layer by impregnating the organic faeces-sensitive material into the nonwoven material layer 1030. Thus the adhesive layer 1070 can be omitted in this embodiment.

In use of the faecal detection sensor 1000, and before the organic faeces-sensitive material layer 1030 has come into contact with any faecal matter, the electrical property of the sensor that dominates the electrical characteristics of the element or circuit comprising the electrodes 1020, 1025 between the faecal detection sensor terminals 1040, 1045 is capacitance. Therefore, the impedance between the faecal detection sensor electrodes 1020, 1025, as for example measured between the faecal detection sensor terminals 1040, 1045, is of a reactive nature, and more specifically, one with a phase angle that is very close to negative ninety degrees.

When the organic faeces-sensitive material layer 1030 comes into contact with faecal matter, the organic faeces-sensitive material layer 1030 reacts to the presence of the enzymes, or other targeted components, that are present in the faecal matter. In embodiments, the reaction of the organic faeces-sensitive material layer 1030 allows for various electrolytes to come into contact with the electrodes 1020, 1025, changing the electrical properties that characterise the element or circuit comprising the electrodes 1020, 1025 between the faecal detection sensor terminals 1040, 1045, from a highly capacitive one, to one that is much more conductive, and in turn moving the phase angle of the impedance between the faecal detection sensor electrodes towards 0 degrees, while at the same time reducing the magnitude of the said impedance.

The organic faeces-sensitive material layer 1030 has a thickness between 10 nanometres to 1 millimetre. The thickness of the organic faeces-sensitive material layer 1030 can be optimised to detect the presence of faecal matter within an acceptable time from discharge (faecal event). The acceptable time (to minimise skin integrity issues and related infections) is less than 60 minutes or less than 30 minutes or less than 10 minutes or less than 5 minutes. In some embodiments, the organic faeces-sensitive material layer 1030 has a thickness between one micrometre and 100 micrometres.

Before the organic faeces-sensitive material layer 1030 has come into contact with any faecal matter, the electrical property of the sensor that dominates the electrical characteristics of the element or circuit comprising the electrodes 1020, 1025 between the faecal detection sensor terminals 1040, 1045 is capacitance. This is because the organic faeces sensitive material layer 1030 acts as a dielectric and once an electrolyte, such as faecal matter, urine or sweat, comes into contact with the faeces sensitive material layer, the electrodes 1020, 1025, the organic faeces sensitive material layer 1030 and the electrolyte form a variable electrolytic capacitor. The capacitance or voltage characterising the element or circuit comprising the electrodes 1020, 1025 between the faecal detection sensor terminals 1040, 1045 changes. Over time, as the organic faeces-sensitive material layer 1030 reacts to the presence of the enzymes, or other targeted components, that are present in the faecal matter the capacitance or voltage characterising the element or circuit comprising the electrodes 1020, 1025 between the faecal detection sensor terminals 1040, 1045 changes further still. This is because the permittivity and/or the geometry of the dielectric material, which is comprised of the organic faeces sensitive material layer 1030, changes as it reacts. Accordingly, in an embodiment the sensor 1000 of FIG. 1 change in capacitance is measured to detect the presence of faecal material coming into contact with the faecal sensitive material layer.

In embodiments, the faecal detection sensor 1000 may also be configured to detect a urinary event and distinguish a urinary event from a faecal event. When there is a urinary event the impedance between the faecal detection sensor electrodes 1020, 1025 stays capacitive, the magnitude of the impedance between the faecal detection sensor electrodes 1020, 1025 decreases, and no faecal event is detected after a certain elapsed interval of time after the magnitude of the impedance between the faecal detection sensor electrodes 1020, 1025 decreases.

Figure 2B:
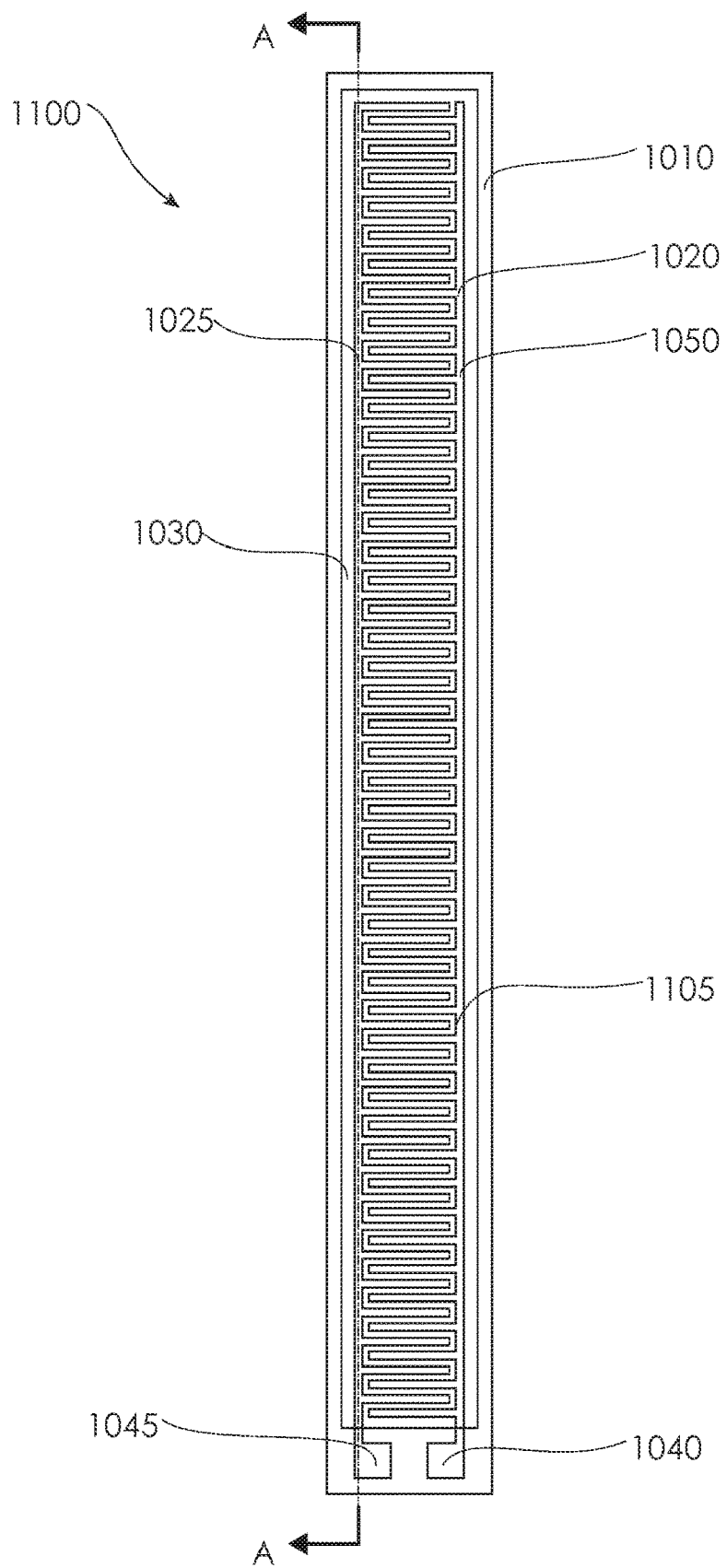
FIG. 2B illustrates a schematic plan view of a faecal detection sensor in accordance with an embodiment of the invention comprising a pair of electrodes on a substrate that are electrically insulated from each other by a durable insulator and also by an outer-most layer of organic faeces-sensitive material which, upon reaction to faecal matter, results in a change in electrical capacitance between the electrodes.

Referring to FIG. 2B, there is shown a faecal detection sensor 1100 in accordance with another embodiment of the invention. The cross-sectional view of the faecal detection sensor 1100 is not shown, but is similar to the cross-sectional view of the faecal detection sensor 1000 that is shown in FIG. 2. In contrast to the faecal detection sensor 1000 of FIG. 2, the faecal detection sensor 1100 of FIG. 2B incorporates a durable insulator 1105 covering the sensor electrodes 1020, 1025 that does not substantially react to the presence of faecal matter and preferably also does not react to the presence of urine or sweat. The durable insulator 1105 may be applied as a sheath or as a layer to cover the electrodes 1020, 1025. The insulator 1105 is covered, at least in part, by the faeces-sensitive material layer 1030 that reacts due to the presence of a faecal enzyme and/or other constituents of faecal matter not present in urine and sweat. Accordingly, the organic faeces-sensitive material layer 1030 indirectly covers, at least in part, the electrodes 1020, 1025. The durable insulator 1105, and any remaining part of the organic faeces sensitive material layer 1030, act as a dielectric and the faecal matter, and any other matter such as urine or sweat, acts as an electrolyte thereby forming, together with the electrodes 1020, 1025, a variable electrolytic capacitor. In this embodiment, the electrical property exhibited by the sensor 1100 that principally changes following the reaction of the organic faeces-sensitive material 1030 is capacitance or voltage. This change in the measured capacitance or voltage is, at least in part, to a change in permittivity and/or geometry of the organic faeces sensitive material layer 1030 acting as a dielectric due to its reaction in the presence of faecal matter.

With respect to the embodiment of the sensor 1100 of FIG. 2B, the processor 184, alone or in combination with another remotely located processor, determines and/or measures one or more electrical properties of the element or circuit comprising the electrodes 1020, 1025 between the faecal detection sensor terminals 1040, 1045, particularly capacitance or voltage. In use of the faecal detection sensor 1100, and before the organic faeces-sensitive material layer 1030 has come into contact with any faecal matter, the electrical property of the sensor that dominates the electrical characteristics of the element or circuit comprising the electrodes 1020, 1025 between the faecal detection sensor terminals 1040 is capacitance. Therefore, the impedance between the faecal detection sensor electrodes 1020, 1025, as for example measured between the faecal detection sensor terminals 1040, 1045, is of a reactive nature, and more specifically, one with a phase angle that is very close to negative ninety degrees.

When the organic faeces-sensitive material layer 1030 comes into contact with faecal matter, the organic faeces-sensitive material layer 1030 reacts to the presence of the enzymes, or other targeted components, that are present in the faecal matter. The reaction and resultant permittivity and/or geometry change of the organic faeces-sensitive material layer 1030 allows for various electrolytes in the faecal matter or other matter such as urine or sweat to influence, to a greater degree, the capacitance measurement between the electrodes 1020, 1025. The provision of the insulator 1105 prevents the faecal or other matter such as urine or sweat from directly contacting and becoming a conductor between the electrodes 1020, 1025.

In the embodiment of FIG. 2B above, the faeces-sensitive material layer 1030 and the durable insulator layer 1105 together may act as a dielectric and the faecal matter, urine or sweat, act as the electrolyte thereby forming, together with the electrodes 1020, 1025, a variable electrolytic capacitor. In this embodiment, the electrical property exhibited by the sensor 1100 that principally changes following the reaction of the organic faeces-sensitive material 1030 is capacitance or voltage. Over time, as the organic faeces-sensitive material layer 1030 reacts to the presence of the enzymes, or other targeted components, that are present in the faecal matter the capacitance or voltage characterising the element or circuit comprising the electrodes 1020, 1025 between the faecal detection sensor terminals 1040, 1045 changes further still. This is because the permittivity and/or the geometry of the dielectric material, which may be comprised of the organic faeces sensitive material layer 1030, changes as it reacts.

Figure 3:
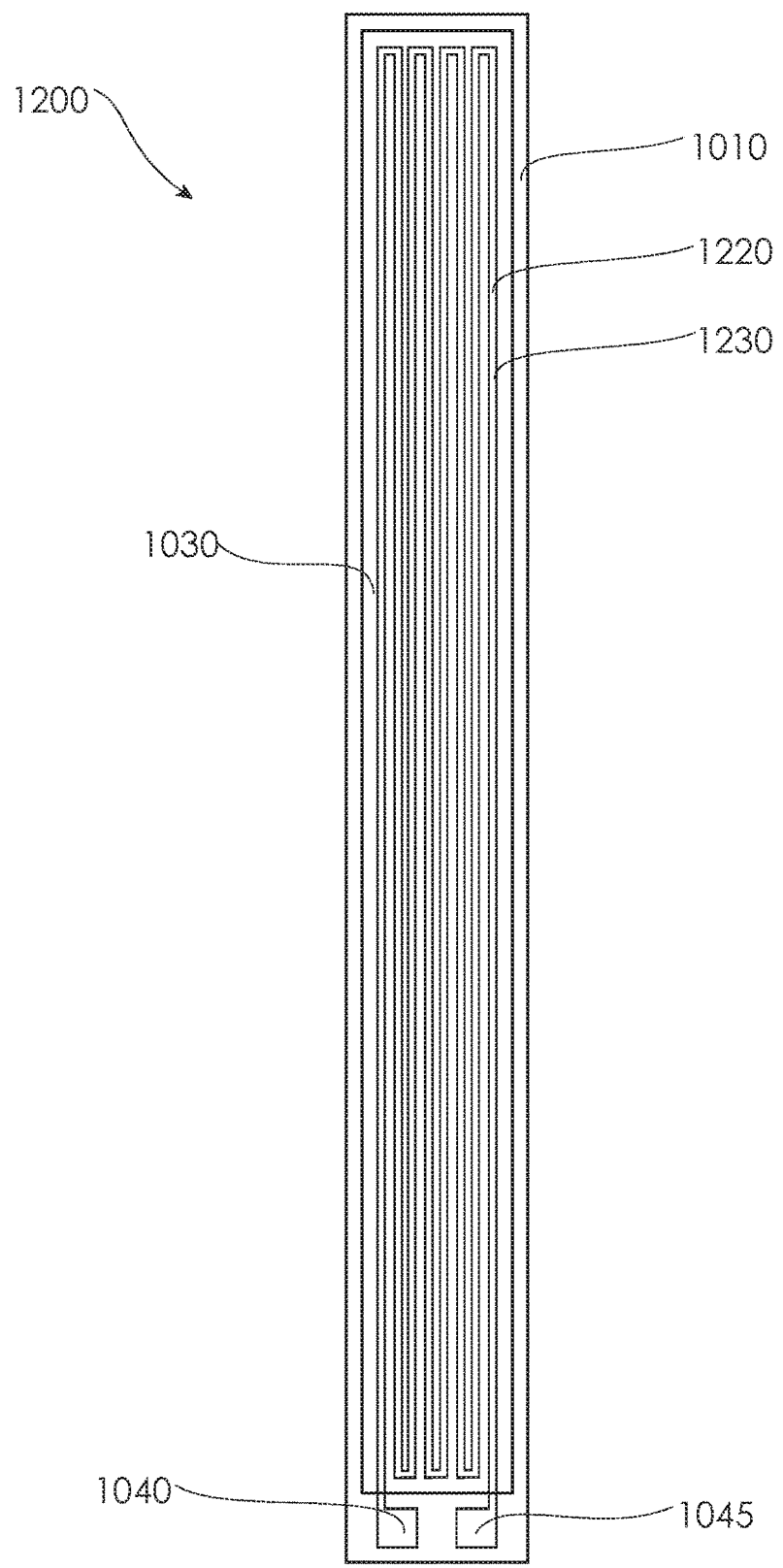
FIG. 3 illustrates a schematic plan view of a faecal detection sensor in accordance with another embodiment of the invention comprising an electrical conductor comprised of a faeces sensitive metallic material on a substrate covered by an organic faeces-sensitive material which, upon reaction to faecal matter, results in a change in an electrical property of the faeces sensitive metallic conductor.

FIG. 3 shows a schematic representation of another embodiment of a faecal detection sensor 1200 in accordance with the invention. The cross-sectional view of the faecal detection sensor 1200 is not shown, but it is essentially similar to the cross-sectional view of the faecal detection sensor 1000 shown in FIG. 2. Analogous to the faecal detection sensor 1000, the faecal detection sensor 1200 optionally incorporates the nonwoven layer 1060, the adhesive layer 1070, and the adhesive layer 1080, but for the sake of clarity, these layers have not been shown in FIG. 3.

The faecal detection sensor 1200 is fabricated on a faecal detection sensor substrate 1010. The faecal detection sensor substrate 1010 comprises a layer of an organic polymer. In some embodiments, the faecal detection sensor substrate 1010 is a layer with a thickness in a range from 10 micrometres to 1500 micrometres. In some embodiments of the invention, the faecal detection sensor substrate 1010 is a layer of poly(ethylene terephthalate) (PET) with a thickness in a range from 50 micrometres to 500 micrometres. In a preferred embodiment of the invention, the faecal detection sensor substrate 1010 is a layer of poly(ethylene terephthalate) (PET) with a thickness in a range from 100 micrometres to 200 micrometres.

The faecal detection sensor 1200 comprises a conductive element in the form of a conductive pattern 1220 fabricated as part of a conductive layer 1230 on the top surface of the faecal detection sensor substrate 1010. As is depicted here, the conductive pattern 1220 has a serpentine geometry. However, the geometry of the conductive pattern 1220 does not have to be limited to that of a serpentine pattern and can be of other suitable geometries. Also incorporated in the conductive layer 1230 is a plurality of faecal detection sensor terminals 1040, 1045. Each end of the conductive pattern 1220 is in electrical contact with a respective one or more of the faecal detection sensor terminals 1040, 1045.

In one embodiment, the conductive pattern 1220 of the conductive layer 1230 is fabricated by screen-printing the conductive pattern 1220 on the top surface of the substrate 1010 and then curing the conductive pattern 1220. In another embodiment, the conductive pattern 1220 is fabricated via piezoelectric inkjet printing of the conductive layer and subsequent UV curing of the layer. In yet another embodiment, the conductive pattern 1220 is fabricated via evaporation and patterning of the conductive pattern 1220 or via sequential evaporation and patterning of a plurality of the conductive patterns 1220 on the top surface of the faecal detection sensor substrate 1010.

In embodiments, the conductive pattern 1220 has a thickness in a range from 10 nanometres to 200 micrometres. In embodiments, the conductive pattern 1220 has a thickness in a range from 50 nanometres to 100 nanometres. Preferably, the conductive pattern 1220 contains silver with a thickness in a range from 10 nanometres to 100 nanometres.

The conductive pattern 1220 is comprised of a metallic conductive, faeces-sensitive material that reacts to faecal constituents. The conductive pattern 1220 can be comprised of a conductive, metallic faeces-sensitive material that does, or does not, react to other bodily fluids like urine and sweat. In preferred embodiments of the invention, the conductive pattern 1220 comprises material that is selected to react to sulfur-containing compounds that are present in faecal matter including, for example, methanethiol, dimethyl disulfide, dimethyl trisulfide, and/or $H_2S$. In preferred embodiments of the invention, the conductive pattern 1220 is comprised of silver or an alloy that contains silver, which react to sulfur-containing compounds.

Accordingly, in some embodiments of the invention, the conductive pattern 1220 alone comprises the preferably metallic faeces sensitive material of the invention whereas in other embodiments a preferably organic faeces-sensitive material covers, at least in part, the metallic faeces sensitive conductive pattern 1220. In the embodiment illustrated in FIG. 3, the faeces sensitive conductive pattern 1220 is covered by another organic faeces-sensitive material layer 1030 that includes an insulator material that reacts to a faecal enzyme and/or other faecal constituents but is substantially insensitive to other bodily fluids, like, urine and sweat. The organic faeces-sensitive material layer 1030 can be selected to react to the lipase enzymes that are present in the faecal matter and can include a lipid. The organic faeces-sensitive material layer 1030 can include a triglyceride and can include tristearin (glyceryl tristearate, 1,3-di(octadecanoyloxy)propan-2-yl octadecanoate). Other faeces-sensitive materials could be used in the organic faeces-sensitive material layer 1030, designed to react with one or more specific components within faeces. Accordingly, in the embodiment of FIG. 3 the conductive pattern forms, at least in part, the faeces sensitive material of the invention.

Embodiments of the invention may include faeces sensitive material comprised only of the conductive pattern 1220 not covered by any other faeces sensitive material layer. In such embodiments, the conductive pattern 1220 may be exposed to air and light and to any other gases or substances which may be present in an absorbent article such as urine, sweat or emitted therein or therefrom such as flatus. However, because the sulfur content of sweat and/or urine and/or flatus is typically orders of magnitude lower than faecal matter only the presence of faecal matter will elicit a significant response in the sensor. This is because only the sulfuric concentrations present in faecal matter, as opposed to urine or sweat or flatus, will reach a reactive threshold of the conductive pattern 1220. For the same reason, the presence of sweat or urine or flatus may not cause the sensor to produce a false positive reading.

In embodiments comprising a conductive pattern 1220 of metallic faeces sensitive material covered by a further organic faeces sensitive material layer 1030 the conductive pattern 1220 is substantially protected from urine, sweat or flatus causing a false positive reading in the absence of faecal matter. In embodiments comprising a conductive pattern 1220 of metallic faeces sensitive material not covered by a further faeces sensitive material layer, the conductive pattern may be covered by a protective strip or film of material (not shown) which may be peeled away or otherwise removed prior to use. Without such a protective strip or film, the conductive pattern 1220 may react or otherwise degrade due to exposure to atmosphere and/or light such as by the formation of a metal oxide on the surface of a silver containing conductive pattern 1220.

Faecal matter is not homogeneous and responses indicated by changes in the electrical behaviour of the conductive pattern 1220 will vary due to factors such as evaporating volatile compounds and the quantity and location of faecal matter relative to the conductive pattern 1220. Accordingly, the conductive pattern 1220 should be thin enough and cover an area large enough for a fast reaction from an adequate amount of faeces (e.g. a reaction time in the order of 4 or 5 minutes).

In use, the faecal detection sensor 1200 is attached to a garment, in the manner illustrated in FIG. 2A and described above, which may include an absorbent garment such as a diaper or incontinence garment, worn by a subject, who is being monitored by a system incorporating the faecal detection sensor 1200. The faecal detection sensor 1200 is attached to such a garment in such a manner that the organic faeces-sensitive material layer 1030 would come into contact with faecal matter but that the faecal detection sensor terminals 1040, 1045 would not come into contact with any faecal matter.

During use of the faecal detection sensor 1200, and before the organic faeces-sensitive material layer 1030 has come into contact with any faecal matter, the conductive pattern 1220 would be intact. Therefore, the resistance of the conductive pattern 1220, as for example measured between the faecal detection sensor terminals 1040, 1045, is low (the circuit comprising the conductive pattern 1220 is closed).

When the organic faeces-sensitive material layer 1030 comes into contact with faecal matter, the organic faeces-sensitive material layer 1030 reacts to enzymes that are present in the faecal matter. The reaction of the conductive pattern 1220 can occur as a result of a chemical reaction between the material comprising the conductive pattern 1220 and the sulfur-containing compounds that are present in faecal matter including, for example, methanethiol, dimethyl disulfide, dimethyl trisulfide, and/or $H_2S$. The reaction of the organic faeces-sensitive material layer 1030 allows for the faecal matter and/or other faecal constituents and/or various other bodily fluids like urine and sweat, as may be present as part of an incontinence event, to come into contact with the conductive pattern 1220. The coming into contact of the faecal matter, other faecal constituents, and/or various other bodily fluids like urine and sweat with the conductive pattern 1220 causer a reaction with the conductive pattern 1220 thereby changing the electrical resistance of the conductive pattern 1220, as for example measured between the faecal detection sensor terminals 1040, 1045, to a higher value, signalling the existence of a faecal event. The conductive pattern 1220 could take on many alternative designs and exhibit different changes in electrical properties, however regardless of the conductive pattern 1220 or element design, the change in state of its electrical properties are the direct result of the organic faeces-sensitive material layer 1030 having broken down by reacting in the presence of faecal material. The chemical reactions involved in the reaction of the conductive pattern 1220 can continue and potentially open the circuit comprising the conductive pattern 1220.

The organic faeces-sensitive material layer 1030 can have a thickness between 10 nanometres to 1 millimetre to facilitate detection of the presence of faecal matter within an acceptable time from discharge (faecal event), wherein the acceptable time (to minimise skin integrity issues and related infections) is less than 60 minutes, or less than 30 minutes, or less than 10 minutes, or less than 5 minutes.

Figure 4:
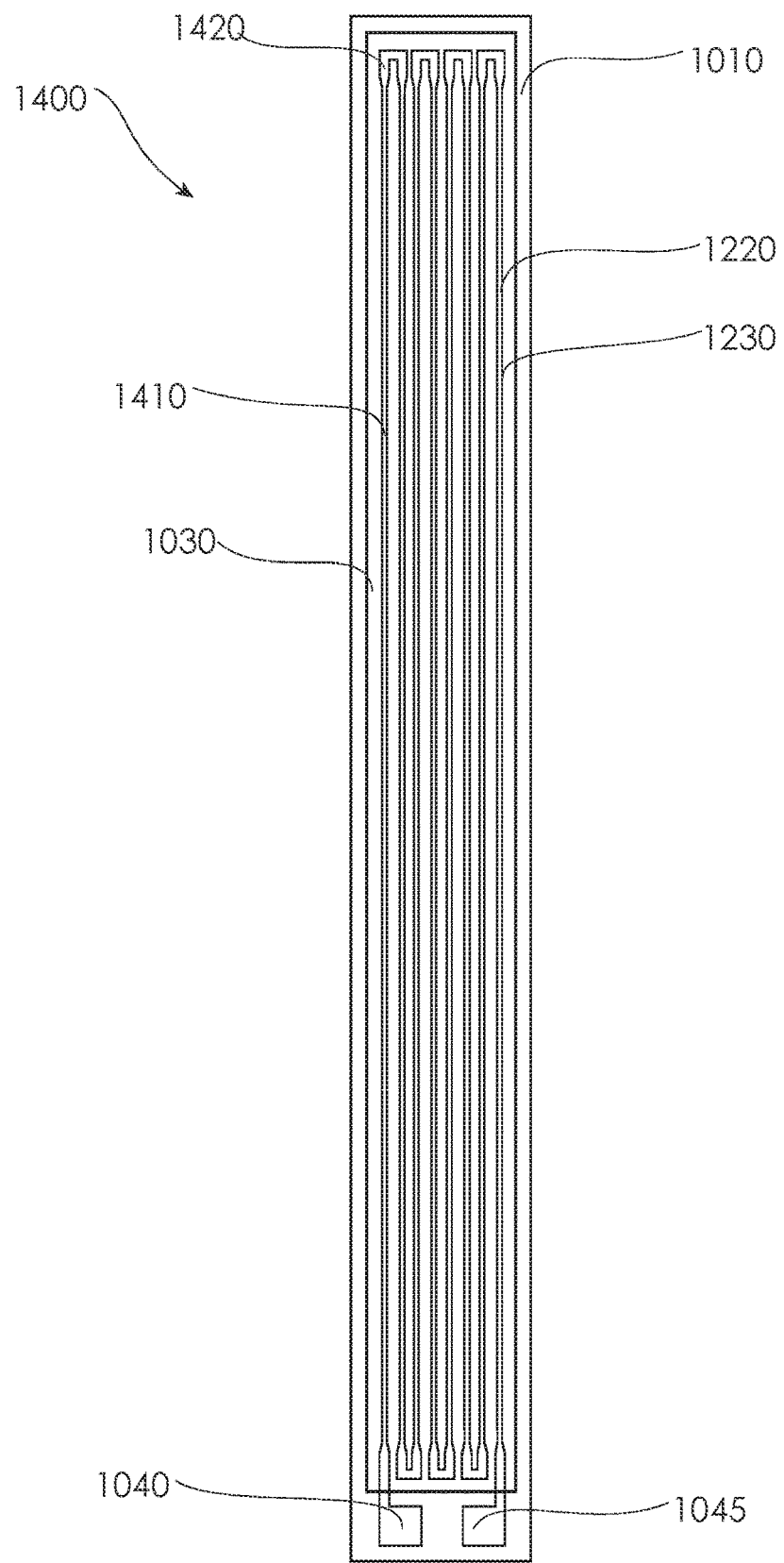
FIG. 4 illustrates a schematic plan view of a faecal detection sensor in accordance with another embodiment of the invention comprising a metallic faeces-sensitive electrical conductor on a substrate having regions of reduced cross-sectional width and that is covered by an organic faeces-sensitive material which, upon reaction to faecal matter, results in a change in an electrical property of the metallic faeces sensitive conductor.

FIG. 4 illustrates another embodiment of a faecal detection sensor 1400 in accordance with the invention. The cross-sectional view of the faecal detection sensor 1400 is not shown, but it is essentially similar to the cross-sectional view of the faecal detection sensor 1000 that is shown in FIG. 2. Analogous to the faecal detection sensor 1000, the faecal detection sensor 1400 optionally incorporates the nonwoven layer 1060, the adhesive layer 1070, and the adhesive layer 1080, but for the sake of clarity, these layers have not been shown in FIG. 4

The faecal detection sensor 1400 is similar in many respects to embodiments of the faecal detection sensor 1200 of FIG. 3, that is embodiments comprising a faeces sensitive conductive pattern 1220, with or without the organic faeces-sensitive material covering layer 1030, except that the faeces sensitive conductive pattern 1220 comprises one or more narrow sections 1410 and one or more wide sections 1420. Thus, the conductive pattern 1220 includes regions of reduced cross sectional area along its length. The functioning of the faecal detection sensor 1400 of FIG. 4 is similar to the functioning of the faecal detection sensor 1200 of FIG. 3, except that the one or more narrow sections 1410 or regions of reduced cross sectional area will undergo a faster relative reaction as a result of the chemical reactions involved in the reaction of the conductive pattern 1220, providing for a more sensitive sensor design. The one or more wide sections 1420, or regions of greater cross sectional area, will provide for mechanical strength and stability of the conductive pattern 1220. The one or more narrow sections 1410 can have a width of less than 350 micrometres, and the one or more wide sections 1420 can have a width of more than 450 micrometres.

Figure 5:
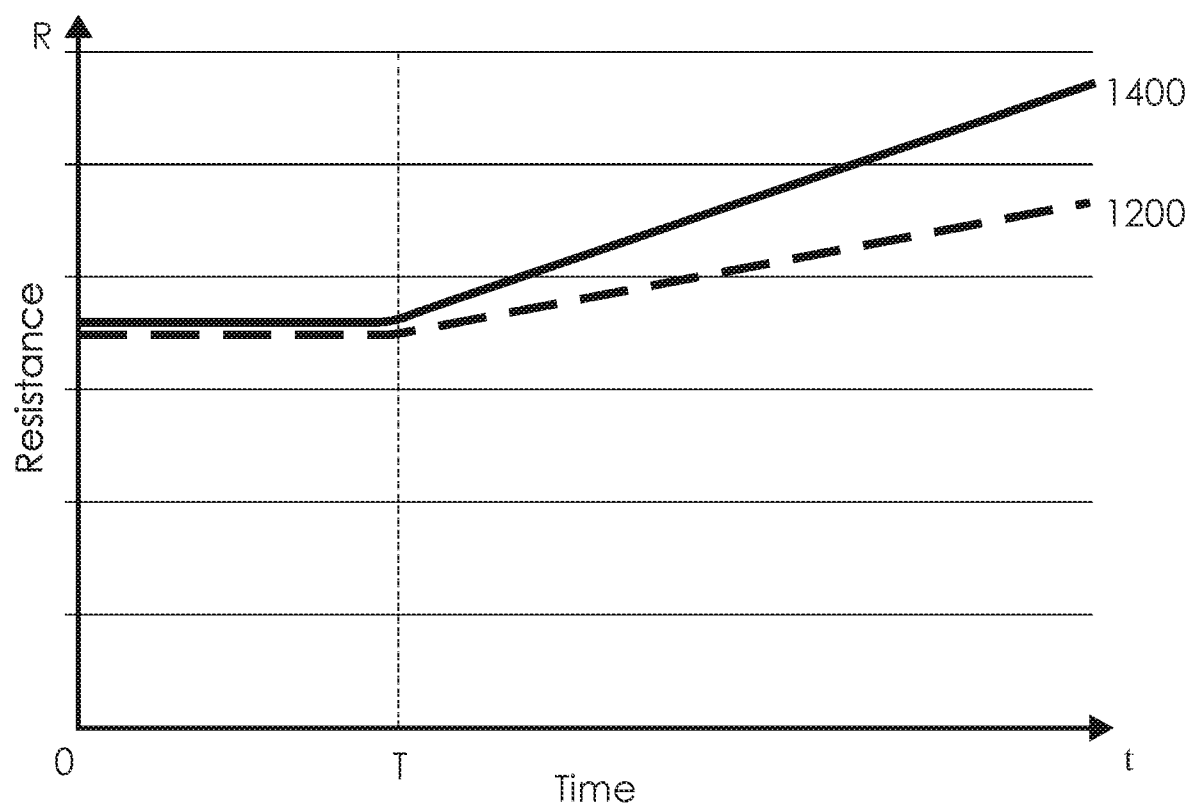
FIG. 5 illustrates a graph plotting resistance over time measured for sensors in accordance with embodiments of the invention wherein upon the presence of faecal matter an increase in electrical resistance of the sensors is exhibited.

The functioning of the embodiments of the faecal detection sensor 1200, 1400 can best be seen in the plot shown in FIG. 5. The resistance of the conductive pattern 1220, as for example measured between the faecal detection sensor terminals 1040, 1045, is shown in the plot as a function of time. At time 0 faecal matter is added on the top of the nonwoven layer 1060, and at a time T, the resistance of the conductive patterns 1220 of each of the embodiments increases substantially. The rate of increase in resistance, which is indicated by the resistance versus time curves in FIG. 5, is different between the sensor embodiments 1200 and 1400. This is due to the conductive pattern 1220 of sensor 1200 reacting relatively less quickly than the conductive pattern 1420 of sensor 1400.

In embodiments of the sensor 1200, 1400 illustrated in FIGS. 3 and 4, the relative change, or the absolute change, in the resistance of the conductive pattern 1220, 1420 (e.g. the percent change) is compared with a suitable threshold, which may be a pre-determined threshold or a dynamic threshold. The relative, or absolute, change in the resistance of the conductive pattern 1220, 1420 exceeding the threshold is indicative of the presence of the faecal matter. The time taken from the initial presence of the faecal matter for the relative, or absolute, change in the resistance of the conductive pattern 1220, 1420 to exceed the threshold is dependent on the type of the faecal matter.

In embodiments, garments can incorporate more than one of the faecal detection sensors 1000, 1200, 1400 described above. Multiple faecal detection sensors can allow for localising the extent of a faecal incontinence event and/or to more easily and/or deterministically determine the volume of a faecal incontinence event.

A further embodiment of the faecal detection sensor (not shown), is comprised of two or more conductive patterns that are electrically insulated from each other via a faeces-sensitive material that acts as an insulator and including a different geometry of the conductive patterns and the faeces-sensitive material namely in the form of a twisted pair of conductive wires where at least one of the conductive wires is insulated with the faeces-sensitive material selected from the materials described above. Also incorporated in this embodiment is two or more faecal detection sensor terminals wherein the conductive pattern is in electrical contact with one or more of the faecal detection sensor terminals.

During use of the faecal detection sensor, and before the faeces-sensitive material has come into contact with any faecal matter, the faeces-sensitive material would be intact. Therefore, the resistance between the conductive patterns, as for example measured between the faecal detection sensor terminals, is high. The resistance is high because the circuit between the faecal detection sensor terminals is open.

When the faeces-sensitive material comes into contact with faecal matter, the faeces-sensitive material reacts with the enzymes that are present in the faecal matter. The reaction of the faeces-sensitive material allows for the conductive patterns to come into mechanical contact with each other thus leading into electrical contact between the conductive patterns. The conductive patterns coming into electrical contact between each other changes the electrical resistance between the conductive patterns, as for example measured between the faecal detection sensor terminals, to a lower value, signalling the existence of a faecal event.

In some embodiments the conductive patterns are sprung or biased in such a way as to further promote a mechanical contact being formed between the conductive patterns upon the reaction of the faeces-sensitive material. Springing or biasing the conductive patterns towards each other promotes a more reliable formation of a lower-resistance electrical contact between the conductive patterns in the presence of faecal matter.

Figure 6:
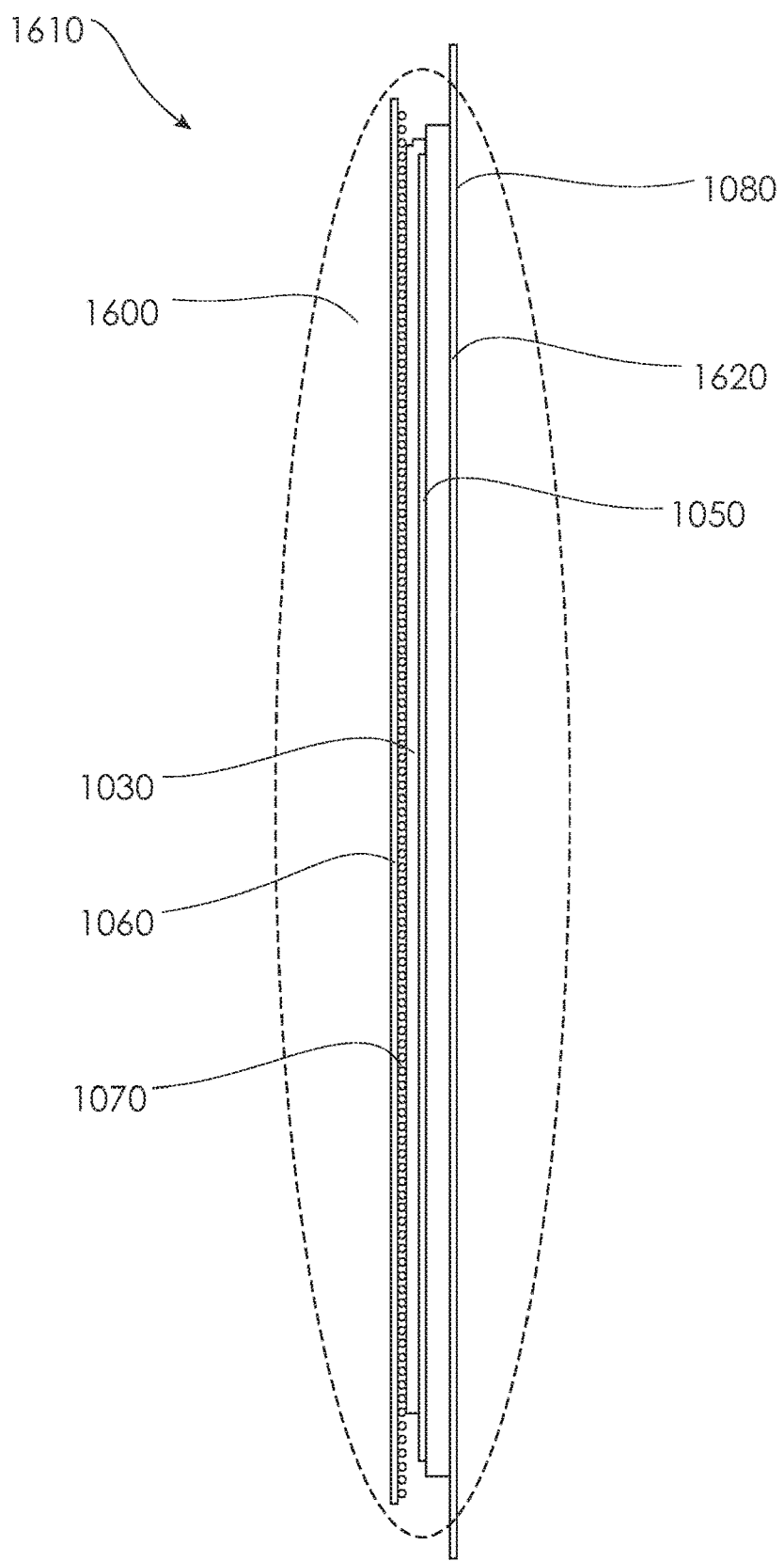
FIG. 6 illustrates a schematic side view of an embodiment of the invention in the form of a peel-and-apply faecal detection sensor that includes the features of any one of the above embodiments and also includes means for attachment to a garment, including a silicone release liner that when peeled away reveals a pressure sensitive adhesive layer for adhering the sensor to an article such as an absorbent article or garment.

Embodiments of the faecal detection sensor 1000, 1200, 1400 can be employed to form what is referred to herein as a peel-and-apply sensor 1600 as illustrated in FIG. 6. The peel-and-apply sensor 1600 is attachable to the garment. The peel-and-apply sensor 1600 is fabricated as part of a peel-and-apply sensor assembly 1610. The fabrication process for the peel-and-apply sensor assembly 1610 will be described later in this description.

FIG. 6 schematically depicts a cross-section of an embodiment of the peel-and-apply sensor assembly 1610. The peel-and-apply sensor assembly 1610 comprises the peel-and-apply sensor 1600 and a substrate 1620. In some embodiments, the substrate 1620 is a disposable substrate. In some embodiments of the invention, the substrate 1620 is a silicone release liner. The top-most layer of the peel-and-apply sensor 1600 optionally comprises the nonwoven layer 1060.

The peel-and-apply sensor 1600 is attached on the top surface of the top layer of a garment wearable by a subject monitored by the system (proximal to the subject). The peel-and-apply sensor 1600 is either attached to the garment during the manufacturing process of the garment, i.e. before they are packaged and distributed, or may alternatively be fitted to the garment after their manufacture. Attachment of the peel-and-apply sensor 1600 to the garment, after manufacture, may be performed manually, or automatically via a suitable apparatus, by peeling the substrate 1620 off the back of the peel-and-apply sensor assembly 1610 to reveal a pressure sensitive adhesive layer 1080 and attaching the peel-and-apply sensor 1600 to the garment. In embodiments, the mechanism of the attachment of the peel-and-apply sensor 1600 to the garment can be via the adhesive layer 1080 or the adhesive layer 1070.

In a preferred embodiment the fabrication process for the peel-and-apply sensor assembly 1610 is based on screen printing technology used in flexible circuits and the like. The peel-and-apply sensor assembly 1610 is built up in a roll-to-roll manufacturing process on the substrate 1620. Optionally one or more insulator layers and one or more conductive layers 1050 are printed onto the substrate 1620, then the barrier layer 1030 is printed, the adhesive layer 1070 is applied over the resultant circuit, and the nonwoven layer 1060 then applied on top of the adhesive layer 1070. Optionally the barrier layer 1030 may already be part of the nonwoven layer 1060 when it is applied to the sensor assembly and in such a case the barrier layer 1030 is not printed. The result is a product that resembles, in many respects, a sensor enabled bandage (i.e. a wound care product). In an alternate embodiment the conductive and insulator materials are inkjet-printed onto the substrate 1620. In yet other embodiments the peel-and-apply sensor circuit is constructed using other lithographic techniques, e.g. photolithographic techniques or gravure printing. The peel-and-apply sensor 1600 is applied directly on top of the garment (rather than inserted under the cover stock or some other location that would require disassembly of the garment or modification to the normal manufacturing process for the garment).

In use, the peel-and-apply sensor 1600 is applied by peeling the substrate 1620 away from the peel-and-apply sensor 1600. The peel-and-apply sensor 1600 is then applied longitudinally down the centre axis of the garment, in the area corresponding with the anal region of the subject, with gentle pressing to ensure that the peel-and-apply sensor 1600 adheres to the garment. The nonwoven layer 1060 that comprises the top layer of the peel-and-apply sensor 1600 points in a direction proximal to the body of the subject being monitored using the system.

One or more resistive layers may optionally be incorporated in the manufacturing process of the peel-and-apply sensor assembly 1610 in place of, or in addition to the various layers that were described as part of the peel-and-apply sensor process above. The resistive layers can provide, as required, a plurality of resistive sensor elements or resistive circuit elements (i.e. resistors) for various sensor or circuit applications. The resistive layer may optionally provide conductive tracks of suitable width, thickness, and length.

One or more of the layers that are incorporated in the peel-and-apply sensor 1610, e.g., the insulator layers, the conductive layers 1050 or the resistive layers can optionally be fabricated via a multipass printing process to achieve a thickness required for a sufficient level of structural strength. The optional resistive layer can be printed in such a way where various features are optionally fabricated with variable number of printing passes, providing for thinner regions with a relatively high sheet resistance and thicker regions with a relatively low sheet resistance.

In accordance with this multipass printing process, the layer is fabricated by using a paste to print a pattern and then repeating the printing step by printing over the previously printed pattern one or more times until a desired thickness has been achieved. Any required curing of the layer can be performed after each printing pass, collectively after the completion of all of the printing passes that are used to create the layer, or only after some of the printing passes. Therefore, the number of printing passes and curing steps do not have to be equal.

In one embodiment of the invention, a printing pass that follows a previous pass is set to generate a pattern that is inset or outset with respect to the said previous pattern to assure a deterministic placement of pattern edges between the two passes.

As the fabrication process for the peel-and-apply sensor assembly 1610 is based on printed flexible circuit technology, and the peel-and-apply sensor assembly 1610 is built up in a roll-to-roll manufacturing process, the per-unit manufacturing cost for the sensor is extremely low. Also, as the peel-and-apply sensor is attached directly on top of the garment (rather than inserted under the cover stock), common, inexpensive types of garments can be used as the process feedstock, with the subsequent attachment of the peel-and-apply sensors to the garments transforming the garments into inexpensive sensor-enabled finished products.

The extremely low cost of the manufactured sensor-enabled products would make it possible for the product to be used to address applications that would not have been considered as economically viable for the utilization of sensor-enabled garments. One of these very cost-sensitive fields of application is the field of 24/7 incontinence management products. One embodiment of this kind of 24/7 incontinence management product comprises a garment with the peel-and-apply sensor attached to it, as described earlier in this specification, to alert a carer that the subject being monitored by the carer requires attention, e.g., for a garment change or manual toileting.

As the per-unit manufacturing cost for the sensor is extremely low it is possible for the product to be used to address the field of childcare. One embodiment of this kind of childcare product comprises a garment with the peel-and-apply sensor attached to the garment as described earlier in this specification. The garment is a garment of the type used in childcare applications, like a baby nappy. This product, instead of being used in an incontinence monitoring application, is used to monitor the normal functioning of a child's faecal habits and to provide warning to a carer in, e.g., a childcare facility, to attend to the child's hygienic requirements and to the need to replace the garment.

The sensor terminals 1040, 1045 of the embodiments of the faecal detection sensor 1000, 1200, 1400, 1600 may also be connected to a wireless radio module (e.g. RFID) to transmit an electrical property wirelessly to the processor module, including the option for the conductive pattern 1220, 1420 to be part of the wireless radio module. In one embodiment, the conductive pattern 1220, 1420 of the conductive layer 1050, 1230 is part of an RFID circuit, such as a tag. The changes in the electrical properties of the conductive pattern 1220, 1420 of the conductive layer 1050, 1230 resulting from an incontinence event modify the characteristics of a resonant circuit in the RFID circuit. In some embodiments of the invention, the wireless coupling between the faecal detection sensor and the processor module is in the form of non-resonant inductive coupling. In some other embodiments, the wireless coupling is in the form of resonant inductive coupling, including for example in the form of near field communication (NFC). In some embodiments of the invention, the wireless coupling is in the form that utilizes far-field electromagnetic propagation.

Figure 7:
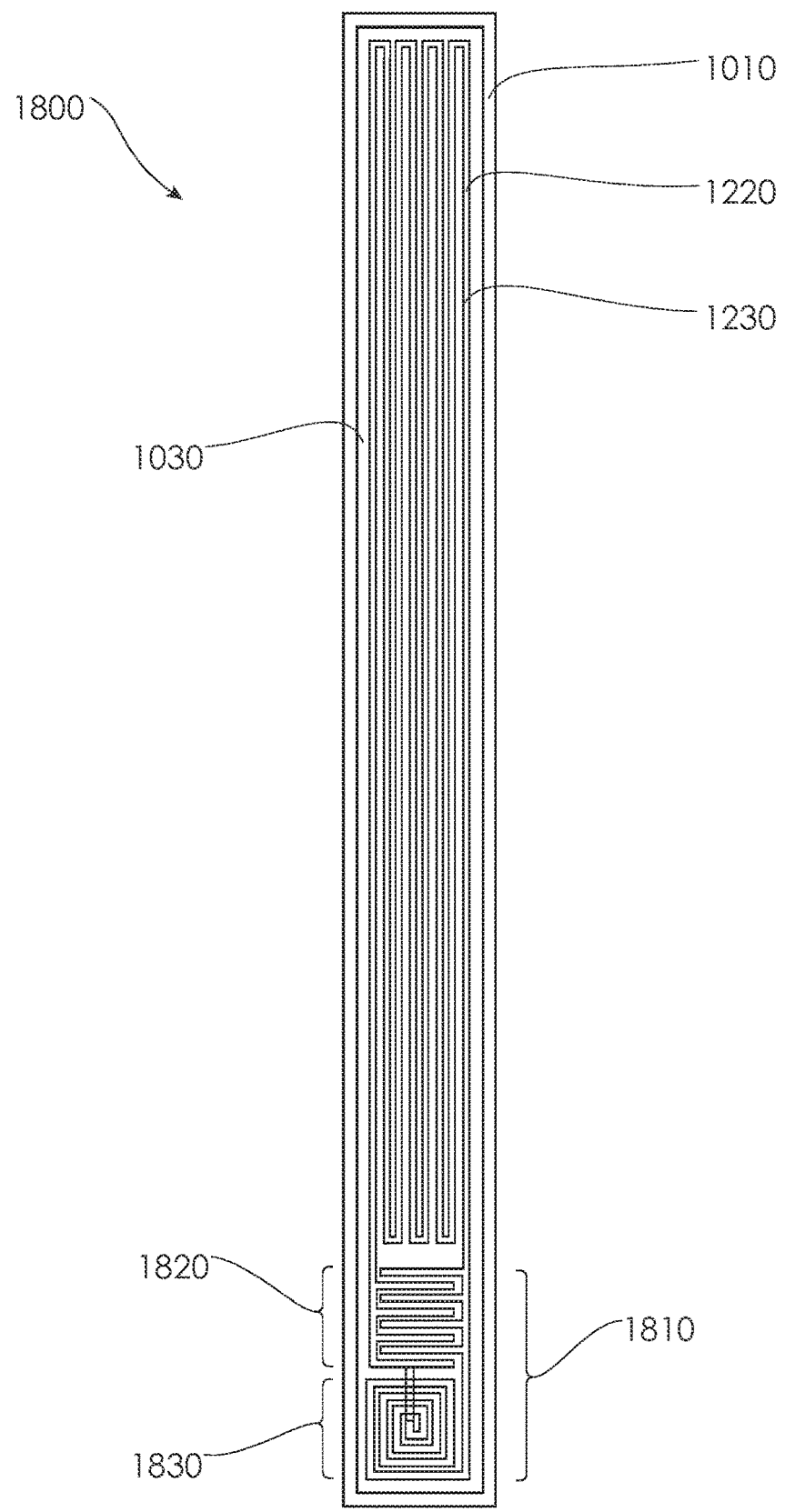
FIG. 7 illustrates a faecal detection sensor in accordance with another embodiment of the invention wherein the sensor includes an metallic faeces sensitive electrical conductor on a substrate covered by an organic faeces-sensitive material which, upon reaction to faecal matter, results in a change in an electrical property of the metallic faeces sensitive conductor and a resonant circuit comprising a capacitive segment and an inductive segment adapted to resonate at a characteristic frequency in response to an interrogating signal from an external interrogating device whereby the resonance characteristic of the resonant circuit is indicative of the electrical property, which changes in the presence of faecal matter.

In FIG. 7 a faecal detection sensor 1800 is depicted which comprises a conductive pattern 1220 in a form corresponding to that which is disclosed in the sensor 1200 of FIG. 3 although it could equally comprise a conductive pattern 1420 in accordance with the sensor 1400 embodiment of FIG. 4. In the faecal detection sensor 1800, the conductive pattern 1220 forms a shunt across a resonant circuit 1810.

The resonant circuit 1810 comprises a capacitive segment 1820, which has substantially capacitive characteristics, and an inductive segment 1830, which has substantially inductive characteristics. During use, the presence of faecal matter will selectively lead into the reaction of the conductive pattern 1220, which will in turn allow the resonant circuit 1810 to resonate at a characteristic frequency, enabling the detection of the said faecal event via, for example, a suitable RF reader or wand.

Figure 8:
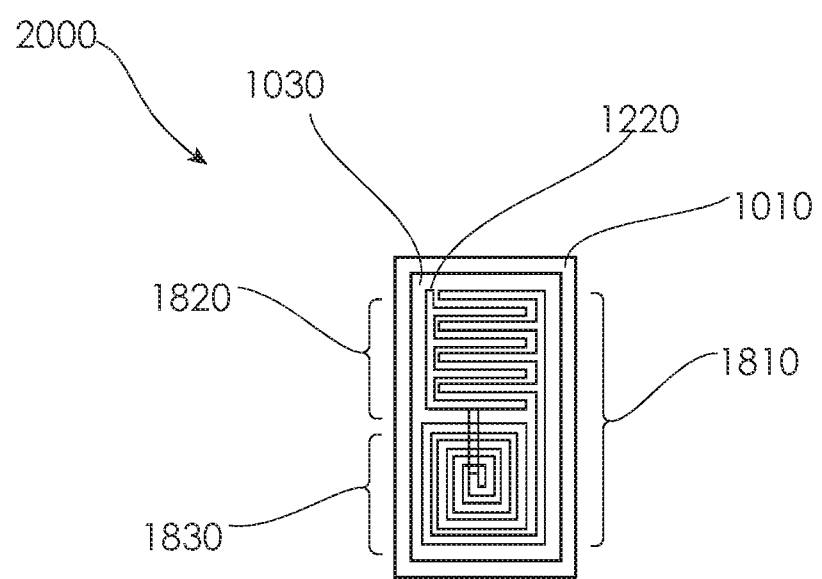
FIG. 8 illustrates a faecal detection sensor in accordance with another embodiment of the invention including a resonant circuit comprising a capacitive segment and an inductive segment adapted to resonate at a characteristic frequency in response to an interrogating signal from an external interrogating device whereby the resonance characteristic of the resonant circuit is indicative of the electrical property, which changes in the presence of faecal matter.

In FIG. 8, a faecal detection sensor 2000 is depicted. The faecal detection sensor 2000 comprises the resonant circuit 1810. The resonant circuit 1810 comprises a capacitive segment 1820, which has substantially capacitive characteristics, and an inductive segment 1830, which has substantially inductive characteristics. During use, the presence of faecal matter will selectively lead into the change in capacitance or resistance between the electrodes 1220, which will in turn degrade or detune the resonance characteristics of the resonant circuit 1810, enabling the detection of the said faecal event via, e.g. a suitable RF wand. The embodiment illustrated in FIG. 8 may comprise a durable insulator that is not susceptible to reaction in the presence of faeces or it may include a faeces sensitive organic layer 1030 covering the sensor electrodes 1220. The durable insulator or and any remaining part of the faeces sensitive material layer 1030, act as a dielectric and the faecal matter, and any other matter such as urine or sweat, acts as an electrolyte thereby forming, together with the electrodes 1220, a variable electrolytic capacitor. The electrical property exhibited by the sensor 2000 that principally changes following the reaction of the faeces-sensitive material 1030 is capacitance or voltage. This change in the measured capacitance or voltage is, at least in part, to a change in permittivity and/or geometry of the faeces sensitive material layer 1030 acting as a dielectric due to its reaction in the presence of faecal matter.

In some embodiments of the invention, more than one of the faecal detection sensor 1000, 1200, 1400, 1600, 1800, 2000 of any one or more of the embodiments described herein are included in a garment where the faeces-sensitive material layer 1030 in at least one of the faecal detection sensor structures in the garment is insensitive to faecal and urinary events. In these embodiments, the detection of a faecal event is via the detection of the differential change in the characteristics of a sensor and the structure comprising the faecal/urinary-insensitive barrier layer.

Figure 9:
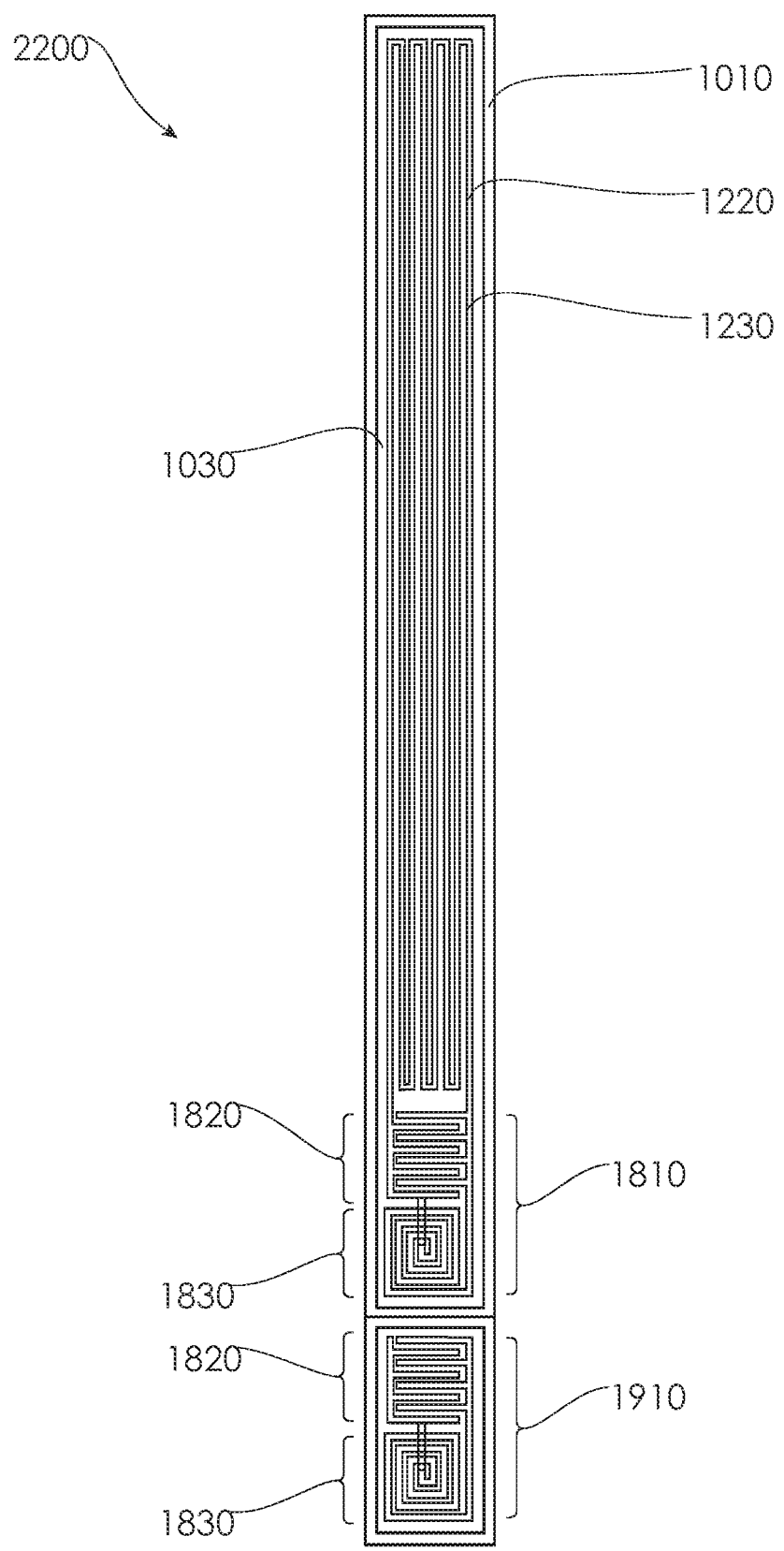
FIG. 9 illustrates a faecal detection sensor in accordance with another embodiment of the invention including two resonant circuits, one of which does not react or otherwise degrade due to the presence of faecal matter or other bodily fluids, thereby incorporating a differential RFID circuit.

Referring to FIG. 9 a faecal detection sensor 2200 is depicted which is similar to the sensor embodiment of FIG. 7 except that it comprises two resonant circuits 1810, 1910, thereby incorporating a differential RFID circuit. The sensor 2200 comprises a conductive pattern 1220 in a form corresponding to that which is disclosed in the sensor 1200 of FIG. 3 although it could equally comprise a conductive pattern 1420 in accordance with the sensor 1400 embodiment of FIG. 4. In the faecal detection sensor 2200, the conductive pattern 1220 forms a shunt across a first one of the resonant circuits 1810, which comprises a capacitive segment 1820 and an inductive segment 1830. The sensor 2200 includes a second resonant circuit 1910 that is also comprised of a capacitive segment 1820 and an inductive segment 1830. The second resonant circuit 1910 is insulated, such as by encapsulation within a durable material that is not susceptible to reaction in the presence of faeces, urine or sweat. During use, the presence of faecal matter will selectively lead to the reaction of the conductive pattern 1220, which will in turn allow the resonant circuit 1810 to resonate at a characteristic frequency or alternatively to detune the resonant circuit 1810 so that is no longer resonates at a characteristic frequency, thereby enabling the detection of the faecal matter via, for example, a suitable RF reader or wand.

It is possible that in use the RF reader will not detect the first resonant circuit 1810. This may be an indication that the resonant circuit 1810 has been detuned due to the reaction of the conductive pattern 1220, which would be indicative of the presence of faecal matter, or it could be due to the resonant circuit 1810 being out of range of the RF reader. Thus, the system may not distinguish between the presence of faecal matter or the resonant circuit 1810 being out of range of the RF reader. The provision of the isolated second resonant circuit 1910 that is not susceptible to reaction in the presence of faeces, urine or sweat, acts as a control or reference resonant circuit 1910. If the RF reader detects the second resonant circuit 1910 and not the first resonant circuit 1810, where the resonant circuits 1810, 1910 are immediately adjacent each other, then this indicates that the resonant circuits 1810, 1910 are within range of the RF reader and that the first resonant circuit 1810 has been detuned as a result of the presence of faecal matter.

The sensor may be included in a garment that the subject is wearing, such as a diaper, or an incontinence related insert, or within bedding that the subject is lying upon. The sensor may be integrated into the garments or fabrics, or other materials that are in proximity to the anal region of the body, or it may be added to such materials in the form of a sensor patch that is designed to adhere to the materials. Detection of a faecal event may enable timely notification to the subject or to a carer to replace the bedding or the diaper that the subject is wearing, to ensure the skin of the subject is clean and clear of any faecal residues, and may be used to inform the status or progress of various bowel conditions. The present invention improves upon the current approach to detection of faecal matter and faecal events occurring with human and animal subjects, and in particular it relies on a reaction between the sensor and the faecal matter to determine if a faecal event has occurred rather than merely inferring that a faecal event may have occurred.

The invention may be susceptible to other modifications or mechanical equivalents without departing from the spirit or ambit of the invention disclosed herein.

The invention claimed is:

1. A faecal detection sensor for an absorbent article, the sensor including:
    at least two conductive electrodes fabricated as part of a conductive layer on a top surface of a faecal detection sensor substrate;
    a faeces-sensitive material insulating, at least in part, the at least two conductive electrodes, wherein the faeces-sensitive material is a lipid, and wherein the sensor exhibits an electrical property that changes following a reaction of the faeces-sensitive material to the presence of a constituent of faecal matter of the absorbent article, wherein the sensor is locatable relative configured to attach to the absorbent article in a location in which the sensor will come into contact with the constituent of faecal matter in the absorbent article while the absorbent article is being worn by a subject, and
    an electronic device including one or more electrical connectors for physical connection with the conductive electrodes for monitoring the electrical property of the electrodes and thereby detecting any change in the electrical property that occurs following the reaction of the faeces-sensitive material.

2. The faecal detection sensor of claim 1, wherein the faeces-sensitive material breaks down due to the presence of the constituent of faecal matter.

3. The faecal detection sensor of claim 1, wherein the reaction of the faeces-sensitive material exposes the at least two conductive electrodes to the constituent of faecal matter or other matter.

4. The faecal detection sensor of claim 1, wherein the faeces-sensitive material reacts to the presence of a lipase.

5. The faecal detection sensor of claim 1, wherein the faeces-sensitive material is comprised of a material that includes a triglyceride.

6. The faecal detection sensor of claim 1, wherein the faeces-sensitive material is comprised of a material that includes tristearin (glyceryl tristearate, 1,3-di(octadecanoyloxy)propan-2-yl octadecanoate) or includes a combination of tristearin and stearic acid.

7. The faecal detection sensor of claim 1, wherein the at least two conductive electrodes are electrically insulated, at least in part, from each other by the faeces-sensitive material.

8. The faecal detection sensor of claim 1, wherein the at least two conductive electrodes are comprised of another faeces-sensitive material that reacts to the presence of another constituent of faecal matter.

9. The faecal detection sensor of claim 8, wherein the another faeces-sensitive material is selected to react to the presence of sulfur-containing compounds including any one or more of methanethiol, dimethyl disulfide, dimethyl trisulfide and hydrogen sulfide.

10. The faecal detection sensor of claim 8, wherein the at least two conductive electrodes comprise silver or an alloy that contains silver.

11. The faecal detection sensor of claim 1, wherein the substrate is a layer of poly(ethylene terephthalate) (PET) with a thickness between 50 micrometres and 500 micrometres.

12. The faecal detection sensor of claim 1, wherein the substrate is a layer of paper or other form of cellulosic material with a thickness in a range of 80 micrometres to 1000 micrometres.

13. The faecal detection sensor of claim 1, wherein the absorbent article is a diaper or incontinence garment.

14. The faecal detection sensor of claim 1, wherein faecal detection sensor electrodes have a mutually interdigitated geometry.

15. A faecal detection sensor for an absorbent article, the sensor including:
    at least two conductive electrodes;
    a durable insulating layer covering the at least two conductive electrodes and a faeces-sensitive material covering, at least in part, the insulating layer and the at least two conductive electrodes, wherein the faeces-sensitive material is a lipid and wherein the sensor exhibits an electrical property that changes following a reaction of the faeces-sensitive material to the presence of a constituent of faecal matter, and wherein the sensor is locatable relative to the absorbent article in a location in which the sensor will come into contact with the constituent of faecal matter in the absorbent article while the absorbent article is being worn by a subject, and
    an electronic device including one or more electrical connectors for physical connection with the conductive electrodes for monitoring the electrical property of the electrodes and thereby detecting any change in the electrical property that occurs following the reaction of the faeces-sensitive material, wherein the presence of the constituent of faecal matter degrades the faeces-sensitive material and the durable insulating layer, and any remaining part of the faces-sensitive material acts as a dielectric, and wherein the electrical property that changes following the reaction of the faeces-sensitive material is a capacitance between the electrodes.

16. The faecal detection sensor of claim 15, wherein the faeces-sensitive material breaks down due to the presence of the constituent of faecal matter.

17. The faecal detection sensor of claim 15, wherein the reaction of the faeces-sensitive material exposes the at least two conductive electrodes to the constituent of faecal matter or other matter.

18. The faecal detection sensor of claim 15, wherein the faeces-sensitive material reacts to the presence of a lipase.

19. The faecal detection sensor of claim 15, wherein the faeces-sensitive material is comprised of a material that includes a triglyceride.

20. The faecal detection sensor of claim 15, wherein the faeces-sensitive material is comprised of a material that includes tristearin (glyceryl tristearate, 1,3-di(octadecanoyloxy)propan-2-yl octadecanoate) or includes a combination of tristearin and stearic acid.

21. A faecal detection sensor for an absorbent article, the sensor including:
  a resonant circuit comprising a capacitive segment and an inductive segment;
  a faeces-sensitive material covering, at least in part, the resonant circuit, wherein the faeces-sensitive material is lipid and wherein the sensor exhibits an electrical property that changes following a reaction of the faeces-sensitive material to the presence of a constituent of faecal matter, wherein the sensor is locatable relative to the absorbent article in a location in which the sensor will come into contact with the constituent of faecal matter in the absorbent article while the absorbent article is being worn by a subject, and
  an electronic device including one or more electrical connectors for physical connection with the resonant circuit for monitoring the electrical property of the resonant circuit and thereby detecting any change in the electrical property that occurs following the reaction of the faeces-sensitive material.

22. The faecal detection sensor of claim 21, wherein the resonant circuit that is adapted to resonate at a characteristic frequency in response to an interrogating signal from an external interrogating device, and wherein the resonant characteristic of the resonant circuit is indicative of the electrical property, which changes following the reaction of the faeces-sensitive material in the presence of the constituent of faecal matter.

23. The faecal detection sensor of claim 21, wherein the faeces-sensitive material breaks down due to the presence of the constituent of faecal matter.

24. The faecal detection sensor of claim 21, wherein the faeces-sensitive material exposes the resonant circuit to the constituent of faecal matter or other matter.

25. The faecal detection sensor of claim 21, wherein the faeces-sensitive material reacts to the presence of a lipase.

26. The faecal detection sensor of claim 21, wherein the faeces-sensitive material is comprised of a material that includes a triglyceride.

27. The faecal detection sensor of claim 21, wherein the faeces-sensitive material is comprised of a material that includes tristearin (glyceryl tristearate, 1,3-di(octadecanoyloxy)propan-2-yl octadecanoate) or includes a combination of tristearin and stearic acid.

\* \* \* \* \*